United States Patent
Zheng et al.

(10) Patent No.: US 9,658,170 B2
(45) Date of Patent: May 23, 2017

(54) TDI IMAGING SYSTEM WITH VARIABLE VOLTAGE READOUT CLOCK SIGNALS

(71) Applicant: KLA-Tencor Corporation, Milpitas, CA (US)

(72) Inventors: Guowu Zheng, Cupertino, CA (US); Jehn-Huar Chern, Fremont, CA (US); Binu Balakrishnan Sathy, Fremont, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 346 days.

(21) Appl. No.: 14/308,383

(22) Filed: Jun. 18, 2014

(65) Prior Publication Data

US 2015/0002655 A1    Jan. 1, 2015

Related U.S. Application Data

(60) Provisional application No. 61/839,768, filed on Jun. 26, 2013.

(51) Int. Cl.
*G01N 21/95* (2006.01)
*H04N 5/372* (2011.01)
*H04N 5/378* (2011.01)

(52) U.S. Cl.
CPC ......... *G01N 21/9501* (2013.01); *H04N 5/378* (2013.01); *H04N 5/37206* (2013.01)

(58) Field of Classification Search
CPC ........... G10N 21/9501; H04N 5/37206; H04N 5/378; G06T 2207/30148
See application file for complete search history.

(56) References Cited

U.S. PATENT DOCUMENTS 7,952,633 B2    5/2011 Brown et al.
2002/0159052 A1  10/2002 Klooster et al.
(Continued)

FOREIGN PATENT DOCUMENTS

JP   2008521010 A1   6/2008

OTHER PUBLICATIONS

KLA-Tencor Corporation, PCT International Search Report and Written Opinion dated October 17, 2014 for PCT/US2014/044411 (corresponding U.S. Appl. No. 14/308,383), 11 pages.

*Primary Examiner* — Twyler Haskins
*Assistant Examiner* — Fayez Bhuiyan
(74) *Attorney, Agent, or Firm* — Bever, Hoffman & Harms, LLP

(57) ABSTRACT

A Time Delay and Integration (TDI) imaging system utilizing variable voltage readout clock signals having progressively increasing amplitudes defined as a function of pixel row location, where pixel rows positioned to receive/collect/transfer image-related charges at the start of the TDI imaging process are controlled using lower amplitude readout clock signals than pixel rows positioned to receive/collect/transfer image-related charges near the end of the TDI process. The clock signal amplitude for each pixel row is determined by the expected maximum amplitude needed to hold and transfer image charges by the pixels of that row. Multiple (e.g., three) primary phase signals are generated that are passed through splitters to provide multiple identical secondary phase signals, and then drivers having gain control circuitry are utilized to produce voltage readout clock signals having the same phases as the primary phase signals, but having two or more different voltage amplitudes.

20 Claims, 6 Drawing Sheets

(56) References Cited

U.S. PATENT DOCUMENTS

| | | |
|---|---|---|
| 2010/0188655 A1 | 7/2010 | Brown et al. |
| 2011/0116077 A1 | 5/2011 | Chuang et al. |
| 2013/0016346 A1 | 1/2013 | Romanovsky et al. |
| 2015/0229859 A1* | 8/2015 | Guidash ................. H04N 5/374 348/308 |

* cited by examiner

TDI IMAGING SYSTEM WITH VARIABLE VOLTAGE READOUT CLOCK SIGNALS

RELATED APPLICATION

The present application claims priority to U.S. Provisional Patent Application 61/839,768, entitled "Reducing TDI Power Consumption by Changing the Voltage of Vertical Readout Clock Voltage", filed by Zheng et al. on Jun. 26, 2013, which is incorporated by reference herein.

FIELD OF THE INVENTION

The present invention relates generally to the field of electronic imaging, and more particularly to inspection of specimens such as semiconductor wafers and photomasks using Time and Delay Integration (TDI) sensors and associated imaging systems.

BACKGROUND OF THE INVENTION

Semiconductor inspection and metrology involves the use of highly sophisticated imaging systems to inspect the surface of a semiconductor wafer or photomasks used in the fabrication of integrated circuits on semiconductor wafers (collectively referred to as "samples" or "specimens" herein) in order to detect defects that may occur during fabrication. Certain advanced imaging systems used for semiconductor defect inspection can detect defects on the order of 30 nm in size during a full inspection of a 300 mm diameter wafer. Such defects are several orders of magnitude smaller than the wafer itself. Advanced imaging systems exhibiting sufficient throughput for wafer inspection systems and photomask inspection systems typically employ Charge-Coupled Device (CCD) sensors and associated TDI drive electronics, and such imaging systems are referred to herein as TDI imaging systems.

FIG. 6 illustrates a generalized CCD sensor utilized in conventional TDI imaging systems. The sensor include a CCD pixel array forming an imaging region 101 in which the pixels are arranged in horizontal rows and vertical columns 102 (e.g., 256×2048 or larger). CCD sensors typically contain channel stops 103, represented by the solid vertical lines in FIG. 6, that prevent the movement of image charges (photoelectrons) from one column to another within the imaging region 101. Image charge movement is thus restricted along columns 102 (i.e., downward in the vertical direction) toward serial registers 104 disposed along the lower edge of the sensor. When an image charge reaches the last pixel in a column, the image charge is transferred by serial registers 104 horizontally, pixel by pixel, until the charge reaches a read-out stage, from which it is transferred to a read-out amplifier or amplifiers 105. A transfer gate 106 or similar structure typically controls charge movement between the imaging region 101 and serial registers 104. Certain sensors have only one read-out amplifier 105, typically positioned at the end of the serial register 104. Other sensors, such as the one shown in FIG. 6, have multiple read-out amplifiers 105 to decrease the time required to read the contents of the pixels in the serial register.

In a typical TDI imaging system arrangement that utilizes a CCD sensor (such as that shown in FIG. 6), a conveying mechanism (not shown) causes the sample to move relative to the sensor while a lamp, laser beam, or other bright illumination light source (not shown) illuminates the sample (e.g., semiconductor wafer) surface. The reflected light is projected/guided onto the sensor, causing the sensor to generate photoelectrons in the pixels that form image charges representing the amount of received reflected light. The sample is scanned such that image charges, which are generated for each small region of the sample's surface, are collected and transferred from pixel to pixel along each pixel column (e.g., downward along vertical columns 102 in FIG. 6) at generally the same rate at which the sample moves relative to the sensor. The image charge portions for each imaged surface region that are collected at each pixel location are integrated (summed) with the image charge generated in previous pixels, and then the "final" image charges are read-out and processed to generate a magnified image of the sample surface using known techniques.

Semiconductor inspection and metrology require very stable, low-noise light sources to detect small defects and/or make very precise measurements of small dimensions of features on a semiconductor wafer specimen. Currently, UV light sources (i.e. light sources with wavelengths 100-400 nm) are used in state-of-the-art semiconductor inspection and metrology systems because UV wavelengths provide adequate sensitivity to defects and dimensions of features produced by current semiconductor processing fabrication techniques. However, as semiconductor fabrication technology produces even smaller device features, next-generation semiconductor inspection and metrology systems must be provided that are able to image and measure features with higher resolution than is capable today. In order to achieve this higher resolution goal, next-generation semiconductor inspection and metrology systems must utilize light sources having wavelengths below 100 nm (e.g., 13.5 nm). Unfortunately, state-of-the-art TDI imaging systems cannot be easily modified to utilize light sources having wavelengths below 100 nm in part because such light exhibits significantly higher energy that would prevent state-of-the-art TDI imaging systems from generating useful imaging data.

What is needed is a TDI imaging system and operating method that facilitates next-generation semiconductor inspection and metrology using light having wavelengths below 100 nm.

SUMMARY OF THE INVENTION

The present invention is directed to a Time Delay and Integration (TDI) imaging system and method in which a TDI sensor (e.g., a CCD pixel array sensor) is controlled using variable (voltage) amplitude readout clock signals to minimize power consumption and thus heat generation, thereby facilitating the use of the sensor in next-generation semiconductor inspection and metrology systems. The present invention thus addresses one problem encountered in the development of next-generation semiconductor inspection and metrology systems: that light having wavelengths below 100 nm (e.g., 13.5 nm) ionizes gas particles disposed over the specimen surface such that suitable imaging of the specimen features is prevented. One approach for avoiding this ionization problem would be to dispose the specimen, TDI CCD sensor and light source in a vacuum chamber. However, this partial solution produces another problem: namely, the elimination of a gaseous atmosphere surrounding the TDI CCD eliminates a major heat transfer mechanism utilized in conventional systems. That is, without the flow of gas (e.g., air) over heat exchange structures coupled to the TDI CCD, the TDI CCD is subject to heat damage. This problem is further exacerbated by higher energy associated with light having wavelengths below 100 nm. According to the present invention, the readout clock signals transmitted to each pixel in a column have amplitudes defined by (i.e., equal to or slightly greater than) the expected minimum electron level needed to hold and transfer image charges by the pixel's position in the column. Specifically, pixels near the "top" of the column (i.e., pixels utilized at the beginning of the TDI process) are only required to hold and transfer small image charges, so readout clock signals supplied to these "upper" pixels need only have relatively low voltage amplitudes. In contrast, pixels near the "bottom" of the column (i.e., pixels utilized near the end of the TDI process) are required to hold and transfer relatively large image charges, so readout clock signals supplied to these "lower" pixels have relatively high voltage amplitudes. By progressively increasing the readout clock signal amplitudes according to the pixel's column location (i.e., with each pixel receiving readout clock signal amplitudes defined by that pixel's expected maximum electron level), the present invention minimizes sensor power consumption by approximately one-third, thus significantly reducing heat generation by the sensor. Because next-generation semiconductor inspection and metrology systems will likely require disposing the sensor in a vacuum chamber, where conventional convection-based sensor cooling techniques would be ineffective, the reduction of sensor heat generation facilitates the use of existing TDI sensors in next-generation semiconductor inspection and metrology systems by significantly reducing the amount of heat that must be removed from the vacuum chamber.

In accordance with alternate embodiments of the present invention, a TDI imaging system and operating method utilize CCD sensors that are controlled by phase signals in a manner similar to that used in conventional TDI processes. Such sensors include an array of pixels arranged in horizontal rows and vertical columns, where each pixel includes two, three or four gates (typically), and where the gates in each column are configured to transfer image charges from pixel to pixel according to known techniques. Primary phase signals are generated using known techniques (e.g., using FPGAs to generate digital phase values, and digital-to-analog converters to covert the digital values to analog signals), and then splitter circuits split (duplicate) each primary phase signal to provide multiple readout clock signals. For example, when a three-phase CCD clocking technique is used, three primary phase signals are generated and then split into multiple secondary phase signals, where each secondary phase signals has a phase equal to one of the three primary phase signals. The secondary phase signals are then processed as described below such that each secondary phase signal becomes an associated readout clock signal, and then the readout clock signals are then transmitted to the gates of the CCD pixels such that each row of pixels receives an associated set of sets readout clock signals (e.g., each row of three-gate CCD pixels is controlled by a set of three readout clock signals including one (first) readout clock signal having a first phase, one (second) readout clock signal having a second phase, and one (third) readout clock signal having a third phase. The readout clock signals are coordinated with movement of a sample such that an image charge generated by light reflected from a sample region is collected and transferred down the column from pixel to pixel in accordance with known TDI image processing techniques.

According to an aspect of the invention, the readout clock signals are generated by amplifying each of the secondary phase signals using an associated gain-controlled driver such that each readout clock signal has the same phase as the associated amplified secondary phase signal, but has an amplitude that differs from other readout clock signals in accordance with the (vertical) position of the pixel row to which the readout clock signal is applied. Stated differently, the gain-controlled drivers are configured such that at least one upper (first) row of pixels (i.e., a row disposed adjacent to the "upper" (first) end of the sensor columns that receives reflected light early in the TDI process) is controlled by a (first) set of readout clock signals having a relatively low (first) amplitude, and at least one lower (second) row of pixels (i.e., a row disposed adjacent to the lower (second) end of the sensor that receives reflected light near the end of the TDI process) is controlled by a (second) set of readout clock signals having a relatively high (second) amplitude. In one specific embodiment, each row's expected maximum image charge is estimated or otherwise predetermined, and the drivers are controlled during a TDI process such that the readout clock signal amplitude applied to each row is defined by the expected maximum image charge amount for that row. For example, upper rows that are expected to hold/transfer small image charges are controlled by readout clock signals whose amplitudes are equal to or slightly greater than the minimum gate electron level needed to perform the hold/transfer function for the expected small image charge. Conversely, lower rows that are expected to hold/transfer larger (e.g., full well) image charges are controlled by readout clock signals whose amplitudes are equal to or slightly greater than the minimum (e.g., "full well") electron level needed to perform the hold/transfer function for the expected larger image charge. Because the image charges collected/held/transferred near the upper end of the sensor are relatively small, the upper pixel rows are controlled using readout clock signals having an amplitude that is significantly lower (e.g., at least one-half or one-third, depending on whether there are two or three levels, and even lower if more levels are used) than the maximum amplitude of readout clock signals utilized to collect/hold/transfer the image charges in the last row (i.e., at the end of the TDI process), when the image charges are at their maximum level. By providing readout clock signals having lower amplitudes to the upper rows and readout clock signals having higher amplitudes to the lower rows, the present invention significantly reduces sensor power consumption over conventional methods that drive all rows using clock signals having the same amplitude, thereby facilitating the use of existing TDI sensors in next-generation semiconductor inspection and metrology systems by significantly reducing the amount of heat generated by the sensor during TDI processes.

In accordance with alternative specific embodiments of the present invention, readout clock signals having multiple amplitudes that progressively (incrementally) increase either in a continuous ramp pattern (i.e., such that each successive row receives an incrementally larger readout signal amplitude), or in a staircase pattern (i.e., such that associated groups of pixel rows receive readout clock signals whose amplitudes increase in a staircase pattern for each successive group of rows). An advantage to the continuous ramp approach is that this approach maximizes power reduction and minimizes heat generation because each row receives only as much power as is necessary to hold/transfer charges at that row's position. In the staircase approach, the pixel rows are grouped into consecutively arranged "levels", with each level including two or more pixel rows that are connected to a common set of drivers (e.g., by way of a secondary splitter formed on the sensor chip) such that each row of a given level receives the same readout clock signals (i.e., having the same amplitude as every other row of that level). Although the staircase pattern approach incurs minor power loss due to some rows receiving readout clock signal amplitudes that are higher than the minimum gate electron level for that group/level, the staircase approach reduces overall system cost and complexity by reducing the number of drivers and associated pin-out connections from the sensor package, and facilitates using existing sensors. In either the continuous ramp or staircase approaches, at least one intermediate (third) row of pixels (i.e., a row disposed between the upper (first) row and the lower (second) row) receives a readout clock signal set having a different (third) amplitude that is between the lower (first) amplitude applied to the upper row(s) and the higher (second) amplitude that is applied to the lower rows.

Similar to conventional TDI imaging systems, the present invention utilizes an X-Y table or other conveyor mechanism to move a sample relative to the sensor such that light is reflected from the same small region (e.g., a defect region) of the sample's surface during each TDI process, and the reflected light is directed onto each pixel of an associated column. That is, light reflected from the defect region during a first time period is integrated with a previously formed charge to generate a "first" collected charge in a given (first) pixel disposed in the column, and then the "first" collected charge is transferred to a next-sequential (second) pixel in coordination with movement of the sample such that light reflected from the defect region during a subsequent (second) time period is directed into a next-sequential (second) pixel where an associated collected charge is integrated with the transferred/held charge to generate a "second" (larger) collected image charge, which is subsequently passed down the column of pixels in like manner. In accordance with an aspect of the invention, the image charge generation/transfer process involves at least one instance in which the collected charge is transferred from a first pixel controlled by readout clock signals having a lower (first) amplitude to a next-sequential pixel controlled by readout clock signals having a higher (second) amplitude. When the continuous ramp approach is used, this increased amplitude occurs upon each image charge transfer (i.e., from row to row). When the staircase approach is used, the amplitude increase occurs periodically when the image charge is transferred from the last row of one level to the first row of the next-sequential level.

According to a practical embodiment of the present invention, a TDI imaging system utilizes a vacuum chamber to house the sensor, the sample to be inspected, and mechanism (e.g., XY table) for moving the sample relative to the sensor. The vacuum chamber facilitates TDI imaging using ultra-high frequency light (e.g., having a wavelength of 13.5 nm) without producing the ionized gas problem associated with using conventional methods. To minimize heat generation inside the vacuum chamber, the system's drive electronics and readout electronics are disposed outside of the vacuum chamber. In an exemplary embodiment, the drive circuitry includes a field-programmable gate array containing logic configured to generate digital phase values using a plurality of look-up tables, digital-to-analog converters (DACs) and optional first stage amplifiers that convert the digital phase values into primary phase signals, a splitter circuit (or other circuitry) for generating secondary phase signals in accordance with the primary phase signals, and the gain-controlled drive circuits that convert the secondary phase signals into the variable amplitude readout clock signals.

According to a specific embodiment of the present invention, the gain-controlled drive circuits include current feedback amplifiers having non-inverting (first) input terminals coupled to receive the secondary phase signals, output terminal on which the variable amplitude readout clock signals are transmitted, and a digital/analog rheostat connected between the amplifier output terminal and an inverting (second) amplifier input terminal. The rheostat of each gain-controlled drive circuit is configured by an appropriate control value that adjusts the gain that generates the target output voltage amplitude. The use of rheostats (or other analog or digital gain-control circuitry) facilitates precise adjustment of the readout clock signal amplitudes transmitted to each row or level of the sensor.

BRIEF DESCRIPTION OF THE DRAWINGS

These and other features, aspects and advantages of the present invention will become better understood with regard to the following description, appended claims, and accompanying drawings, where:

DETAILED DESCRIPTION OF THE DRAWINGS

Figure 1:
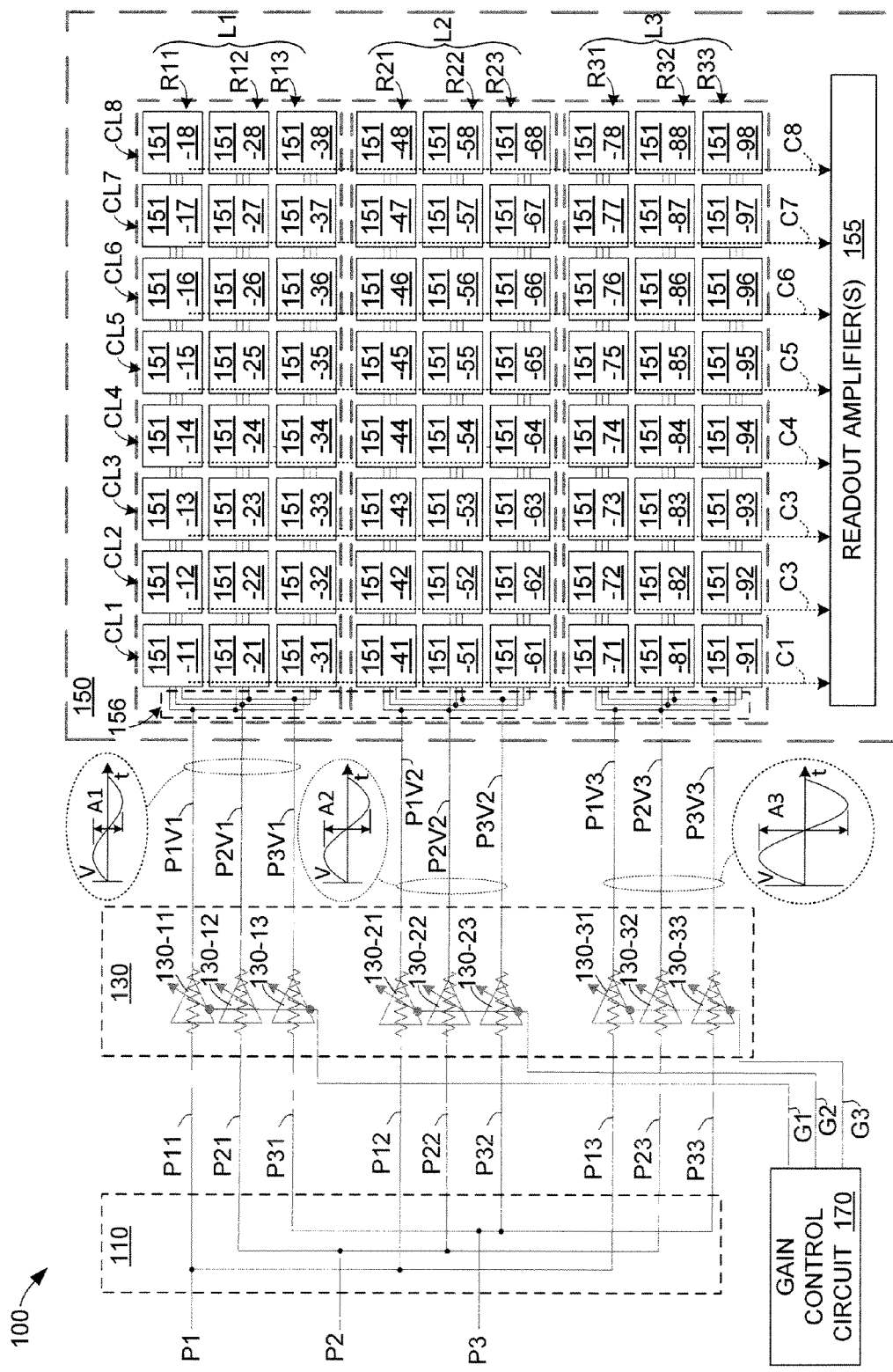
FIG. 1 illustrates a simplified TDI imaging system including a TDI sensor according to an embodiment of the present invention.

The present invention relates to an improvement in TDI image sensing. The following description is presented to enable one of ordinary skill in the art to make and use the invention as provided in the context of a particular application and its requirements. As used herein, directional terms such as "upper", "lower", "downward", "horizontal" and "vertical" are intended to provide relative positions for purposes of description, and are not intended to designate an absolute frame of reference. As used herein, the phrase "readout clock signal" is intended to refer to "vertical" readout clock signals (i.e., readout clock signals utilized to implement charge transfer along columns in a CCD sensor), as opposed to "horizontal" (serial) readout clock signals used to read charges out of the serial registers. The terms "coupled" and "connected", which are utilized herein, are defined as follows. The term "connected" is used to describe a direct connection between two circuit elements, for example, by way of a metal line formed in accordance with normal integrated circuit fabrication techniques. In contrast, the term "coupled" is used to describe either a direct connection or an indirect connection between two circuit elements. For example, two coupled elements may be directly connected by way of a metal line, or indirectly connected by way of an intervening circuit element (e.g., a capacitor, resistor, inductor, or by way of the source/drain terminals of a transistor). Various modifications to the preferred embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed.

The amplitude of readout clock signals defines the maximum charge holding capacity (i.e., the full well capacity) of the CCD pixels, and is one of the major factors defining the power consumption of a TDI imaging system. In traditional applications, the readout clock signals clocks transmitted to a TDI CCD sensor maintain the same amplitude for the entire imaging area (i.e., all pixel rows receive readout clock signals having the same voltage amplitude determined by the full well pixel level, irrespective of the pixel location). Assuming a total charge (or total signal level) of S, after M pixel transfers (i.e., after M rows), the collected charge for each pixel is approximately S/M, and the total hold charge of a pixel in the array is defined by its vertical (row) location and is expressed as:

$$S(y) = \frac{Sy}{M} \quad \text{Equation 1}$$

where y is the pixel position (row number) in the TDI integration direction. Now, considering a CCD with full well level of $S_F$, the maximum charge need to be held in pixel position y becomes:

$$S_F(y) = \frac{S_F y}{M} \quad \text{Equation 2}$$

If the required maximum vertical clock amplitude to hold and transfer this full well charge is $V_{FW}$, then the voltage swing required to hold and transfer in pixel y having charge level $S_F(y)$ also reduces by a factor $$\frac{y}{M}.$$

Using the constant voltage readout clock signals of the conventional method, the normalized power requirement for vertical driver amplifier is expressed as:

$$P = M(V_{FW})^2 \quad \text{Equation 3}$$

The present invention, described as forth below with reference to exemplary practical examples, is distinguishable over the conventional approach in that the present invention introduces the use variable vertical clock amplitude for different pixel rows, defined as a function of pixel row location. Assuming the maximum amplitude to hold and transfer charge of $S_F/M$ is $V_{FW}$, by varying the readout clock signal amplitudes with vertical pixel (row) position, as indicated in FIG. 5(B), the sensor power consumption ($\Sigma fCV^2$) reduces without sacrificing sensor performance because the modified readout clock signal amplitude supplied to each pixel row is sufficient to perform hold and transfer of the maximum possible image charge generated on that pixel row.

Figure 5A:
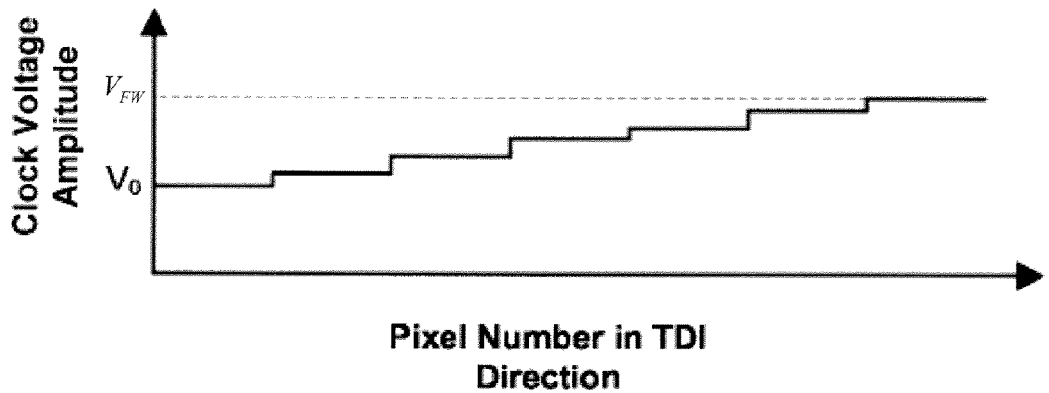
FIGS. 5(A) and 5(B) are diagrams depicting variable readout clock signal amplitudes with continuous ramp and staircase patterns, respectively, according to alternative embodiments of the present invention.
Figure 5B:
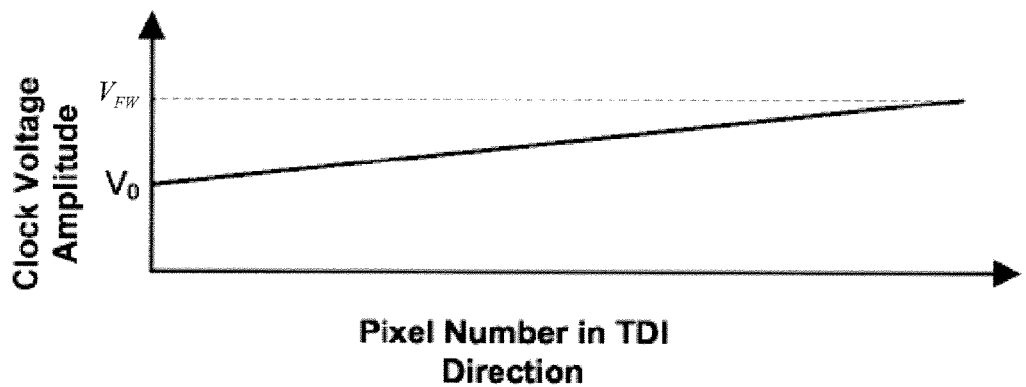

To simplify implementation of the invention, a staircase amplitude increment (indicated in FIG. 5(A), and implemented in the practical embodiments) is used instead of gradual increase of voltage level. The normalized power consumption for the staircase option for every pixel integration level is expressed as $$P' = \sum_{n=1:M} (nV_{min})^2 \quad \text{Equation 4}$$

where n is the number of transfer in TDI direction $V_{min}$ is the expected maximum charge for the first pixel (or the expected maximum photo-electron generated on each TDI integration step) and is given by $$V_{min} = \frac{V_{FW}}{M} \quad \text{Equation 5}$$

Hence the normalized power requirement becomes $$P' = \left(\frac{V_{FW}}{M}\right)^2 \sum_{n=1:M} n^2 \quad \text{Equation 6}$$

and power reduction $$\frac{P'}{P}$$

utilizing the present invention is calculated as:

$$\frac{P'}{P} = \frac{1}{M^3} \sum_{n=1:M} n^2 \quad \text{Equation 7}$$

where P' is the required power consumption using variable vertical clock amplitude. Therefore, the benefits of the present invention include reduced power consumption in comparison with conventional clock scheme (e.g., down to 33.33% as governed by Equation 7), and reduced dark current due to minimized thermal stress on the CCD at reduced power level.

The present invention is now described with reference to certain simplified and practical exemplary embodiments.

FIG. 1 shows a partial TDI imaging system 100 utilizing a simplified three-phase sensor 150 including an array of CCD pixels 151-11 to 151-98 arranged in nine rows R11-R33 and eight columns CL1-CL8. Each row of pixels is connected together such that each pixel of each row receives and is controlled by the same set of three readout clock signals. In addition, in accordance with the exemplary embodiment, the pixel rows are grouped (e.g., by way of splitter circuits 156) to form consecutively arranged levels L1 to L3 such that each level includes three rows that share the same set of three readout clock signals. For example, level L1 includes rows R11 to R13 that receive and are controlled by the same readout clock signal set including readout clock signals P1V1, P2V1 and P3V1 (i.e., each of pixels R11 to R18 in row R11, pixels R21 to R28 in row R12, and pixels R31 to R38 in row R13 receives and is controlled by readout clock signals P1V1, P2V1 and P3V1). Similarly, level L2 includes rows R21 to R23 that receive and are controlled by readout clock signals P1V2, P2V2 and P3V2, and level L3 includes rows R31 to R33 that receive and are controlled by readout clock signals P1V3, P2V3 and P3V3. Those skilled in the art will recognize that the depicted nine-by-eight array is greatly simplified for explanatory purposes, and that actual sensors typically include many more rows and columns. Further, the levels may include any number of rows (one, two, four), and that pixels requiring a different number of readout clock signals (e.g., two or four) may also be used.

TDI imaging system 100 utilizes various circuits to generate three primary phase signals P1, P2 and P3 that are then split and processed to form nine readout clock signals P1V1 to P3V1, P2V1 to P2V3 and P3V1 to P3V3 in a manner similar to that utilized in conventional imaging systems. Referring to the left side of FIG. 1, primary phase signals P1, P2 and P3 are generated using known techniques (e.g., using FPGAs, DACs and amplifiers in the manner described below with reference to FIG. 3) such that primary phase signal P1 is out of phase from phase signals P2 and P3 in a way that produces the desired operation of sensor 150. Primary phase signals P1, P2 and P3 are then respectively "split" (i.e., effectively duplicated) by a splitter circuit 110 to form nine secondary phase signals P11 to P33, each being identical to one of the primary phase signals. That is, secondary phase signals P11 to P33 are identical and have the same phase as primary phase signal P1, secondary phase signals P21 to P23 have the same phase as primary phase signal P2, and secondary phase signals P31 to P33 have the same phase as primary phase signal P3. Secondary phase signals P11 to P33 are then processed by a driver circuit 130 such that each secondary phase signal is amplified by an associated driver 130-11 to 130-33 to generate an associated readout clock signal P1V1 to P3V3. For example, secondary phase signal P11 is applied to an input terminal of driver 130-11, which in turn generates on its output terminal associated readout clock signal P1V1. Similarly, drivers 130-12 and 130-13 respectively convert secondary phase signals P21 and P31 into associated readout clock signals P2V1 and P3V1, drivers 130-21, 130-22 and 130-23 respectively convert secondary phase signals P12, P22 and P32 into associated readout clock signals P1V2, P2V2 and P3V2, and drivers 130-31, 130-32 and 130-33 respectively convert secondary phase signals P13, P23 and P33 into associated readout clock signals P1V3, P2V3 and P3V3. Driver circuit 110 is coupled to corresponding input terminals of sensor 150 such that each driver 130-11 to 130-33 is coupled to an associated pixel row or group of rows. For example, the output terminal of driver 130-11 is coupled to sensor 150 such that rows R11, R12 and R13 receive clock signal P1V1, which is generated in accordance with secondary phase signal P11. Note that drivers 130-21 and 130-31 are also coupled to sensor 150 such that rows R11, R12 and R13 receive clock signal P2V1 and P3V1, which are generated in accordance with secondary phase signals P21 and P31, respectively. That is, each row of pixels (e.g., row R11) is controlled by three phase signals. In one embodiment, readout clock signals P1V1 to P3V3 are generated as continuous clocking signals waveforms according to methods taught in co-owned U.S. Pat. No. 7,952,633 entitled "Apparatus for continuous clocking of TDI sensors" (Brown et al.), which is incorporated herein by reference in its entirety.

According to an aspect of the invention, drivers 130-11 to 130-33 of driver circuit 110 comprise gain-control circuitry that is controlled (e.g., by way of a gain control circuit 170) such that the amplitudes of readout clock signals P1V3 to P3V3 are defined in accordance with the (vertical) position of the pixel row(s) to which readout clock signals are applied, and the applied readout clock signal amplitude increases in the direction in which image charges travel along columns CL1 to CL8. For example, the gain of drivers 130-11 to 130-13 is controlled by way of control signal G1 such that at least one upper (first) row of pixels (in this example, rows R11 to R13, which are disposed adjacent to the end of columns CL1 to CL8 that initiates image charges during a TDI process) receives readout clock signals P1V1, P2V1 and P3V1, where "P1", "P2" and "P3" designate the three phase signals, and "V1" designates a relatively low (first) amplitude A1 that is depicted at the upper central portion of FIG. 1. In contrast, the gain of drivers 130-31 to 130-33 is controlled by way of control signal G3 such that at least one lower (second) row of pixels (e.g., rows R31 to R33 disposed adjacent to the end of columns CL1 to CL8 at which final image charges are transferred/generated during a TDI process) receives readout clock signals P1V3, P2V3 and P3V3, where "V3" designates a relatively high (second) amplitude A3 that is depicted at the lower central portion of FIG. 1, and where amplitude A3 is greater than amplitude A1. To provide readout clock signals that increase in the downward vertical direction, the gain of drivers 130-21 to 130-23 is controlled by way of control signal G2 such that at least one middle (third) row of pixels (e.g., rows R21 to R23 disposed to receive image charges from the upper rows and to transfer the image charges to the lower rows during a TDI process) receives readout clock signals P1V2, P2V2 and P3V2 having an intermediate amplitude A2 (depicted in the central region of FIG. 1) having an amplitude that is between amplitudes A1 and A3.

In one specific embodiment, each row's expected maximum image charge is estimated or otherwise predetermined, and drivers 130-11 to 130-33 are controlled during each TDI process such that the readout clock signal amplitude (i.e., amplitudes A1, A2 and A3) applied to each row is defined by the expected maximum image charge amount for that row. For example, upper rows R11 to R13 that are expected to hold/transfer small image charges are controlled by readout clock signals whose amplitudes A1 are equal to or slightly greater than the minimum gate electron level needed to perform the hold/transfer function for the maximum expected image charge generated in pixels 151-31 to 151-38 of row R13. Conversely, lower rows R31 to R33 that are expected to hold/transfer larger (e.g., full well) image charges are controlled by readout clock signals whose amplitudes A3 are equal to or slightly greater than the minimum electron level needed to perform the hold/transfer function for the expected maximum "full well" image charge amount generated in pixels 151-91 to 151-98 of row R33. Middle rows R21 to R23 are expected to hold/transfer intermediate image charges, and are therefore controlled by readout clock signals whose amplitudes A2 are equal to or slightly greater than the minimum electron level needed to perform the hold/transfer function for the expected maximum intermediate image charge generated in the pixels of row R23. In one embodiment, because the image charges collected/held/transferred in upper rows R11 to R13 (i.e., at the beginning of the TDI process) are relatively small in comparison to those generated in lower rows R31 to R33, amplitude A3 of readout clock signals P1V3, P2V3 and P3V3 are significantly higher (e.g., at least two times higher in the case of two levels, three times higher in the depicted example) than amplitude A1 of readout clock signals P1V1, P2V1 and P3V1 utilized to collect/hold/transfer the image charges in upper rows R11 to R13.

The exemplary embodiment of FIG. 1 utilizes a "staircase" clock distribution in which rows R11-R33 of sensor 150 are grouped into three consecutively arranged levels L1 to L3 such that each level includes three rows (e.g., level L1 includes rows R11 to R13, level L2 includes rows R21 to R23, and level L3 includes rows R31 to R33). In the staircase clock distribution approach, each driver 130-11 to 130-33 is coupled to every row of an associated level L1 to L3 such that every row of the associated level receives the same readout clock signal generated by the driver. For example, driver 130-11 is coupled to every row R11, R12 and R13 of level L1 (e.g., by way of second splitter circuits 156 formed on sensor 150) such that every row R11, R12 R13 receives readout clock signal P1V1. Similarly, drivers 130-12 and 130-13 are coupled to every row R11, R12 and R13 of level L1 such that every row R11, R12 R13 also receives readout clock signals P2V1 and P3V1. In addition, drivers 130-21, 130-22 and 130-23 are coupled to every row R21, R22 and R23 of level L2 such that these rows receive readout clock signals P1V2, P2V2 and P3V2, and drivers 130-31, 130-32 and 130-33 are coupled to every row R31, R32 and R33 of level L3 such that these rows receive readout clock signals P1V3, P2V3 and P3V3. In this way, the rows of each level L1 to L3 is controlled by phase signals having an associated readout clock signal amplitude (e.g., level L1 is controlled using amplitude A1, level L2 is controlled using amplitude A2, and level L3 is controlled using amplitude A3). The staircase clock distribution approach is generally depicted in FIG. 5(A), which indicates readout clock signal amplitudes increasing from a minimum voltage V0 to a maximum voltage $V_{FW}$ in a series of "steps", where each step indicates an associated number of pixel rows that receive readout clock signals having the same amplitude.

Figure 5C:
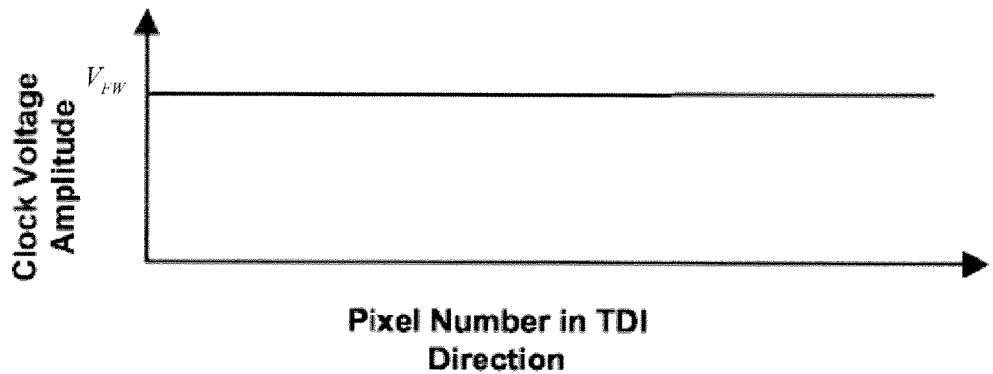
FIG. 5(C) is a diagram depicting conventional constant voltage readout clock signal amplitudes.
Figure 6:
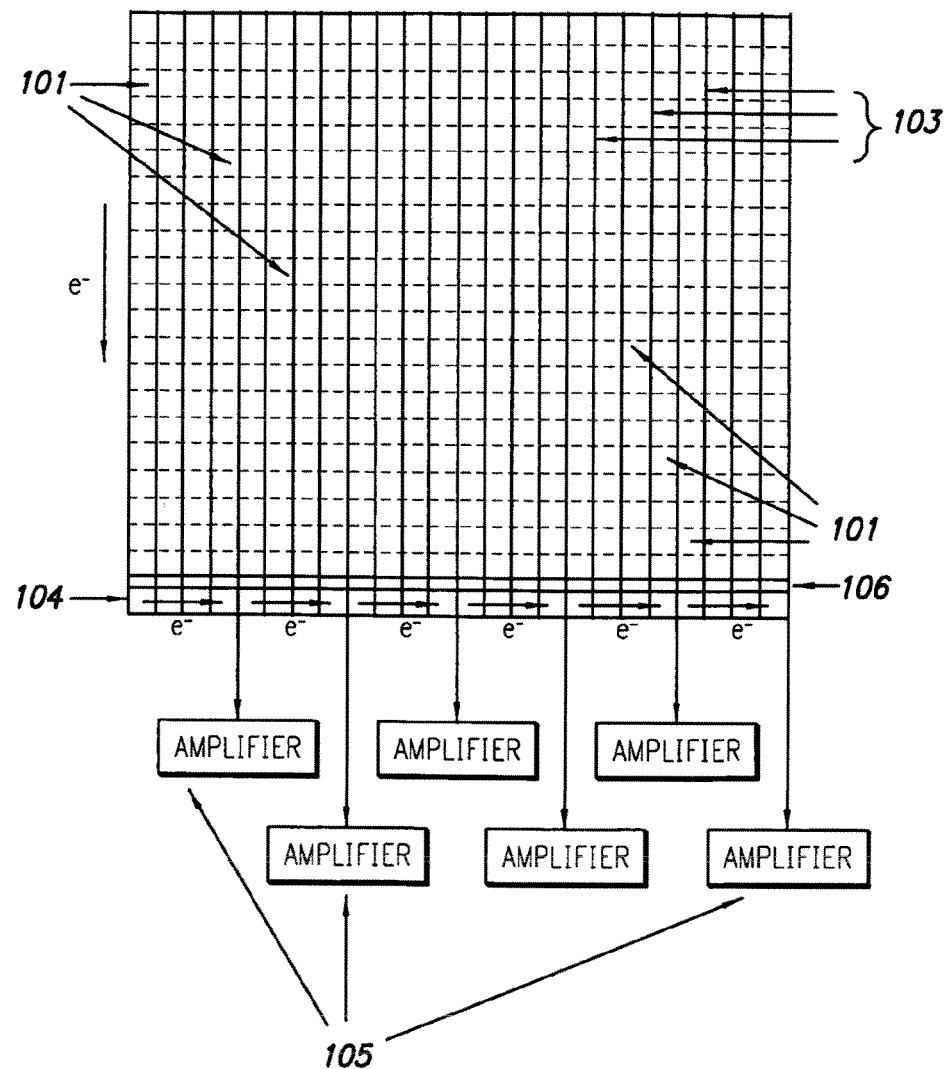
FIG. 6 is a simplified block diagram showing a conventional TDI sensor.

FIG. 5(B) is a diagram illustrating an alternative continuous ramp clock distribution approach in which readout clock signal amplitudes increase at each image charge transfer (i.e., such that each successive row receives an incrementally larger readout signal amplitude). An advantage to the continuous ramp approach is that this approach maximizes power reduction and minimizes heat generation because each row receives only as much power as is necessary to hold/transfer charges at that row's position. In contrast, using the staircase approach, the readout clock signal amplitude is defined by the last pixel row of each level, which requires "upper" rows in each level to be controlled using amplitudes that may be higher than needed. Although the staircase pattern approach incurs minor power loss due to some rows receiving readout clock signal amplitudes that are higher than the minimum gate electron level for that group/level, the staircase approach reduces overall system cost and complexity by reducing the number of drivers and associated pin-out connections from the sensor package, and facilitates using existing sensors. In contrast, as indicated in FIG. 5(C), the conventional approach applies the same readout clock signal maximum amplitude $V_{FW}$ to all sensor pixel rows.

Figure 2:
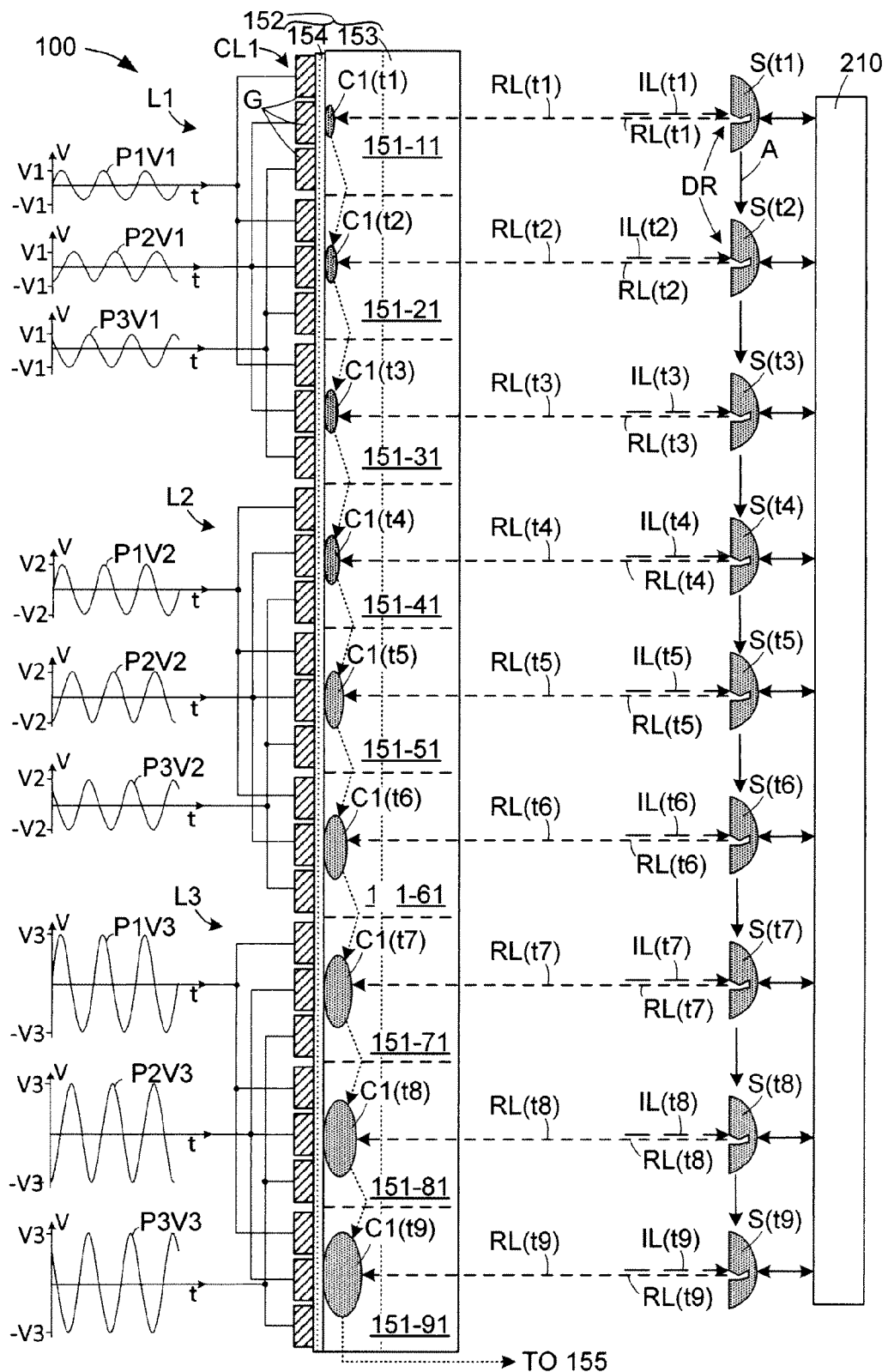
FIG. 2 shows a portion of the TDI imaging system of FIG. 1, and in particular depicts an exemplary image charge as it integrates collected charge and is transferred from pixel to pixel along a column of the TDI sensor during operation.

FIG. 2 is a simplified diagram illustrating a TDI process involving the generation of an image charge C1 in column CL1 of sensor 150 (shown in FIG. 1). Referring to the left side of FIG. 2, exemplary readout clock signals P1V1, P2V1 and P3V1 are shown, each having amplitude A1 that varies between V1 and −V1, are applied to gates G of pixels 151-11, 151-12 and 151-13, respectively. Similarly, exemplary readout clock signals P1V2, P2V2 and P3V2 having amplitude A2 that vary between V2 and −V2 (but having the same phases as readout clock signals P1V1, P2V1 and P3V1, respectively) are applied to the gates of pixels 151-21, 151-22 and 151-23, respectively, and exemplary readout clock signals P1V3, P2V3 and P3V3 having amplitude A3 varying between V3 and −V3 are applied to the gates of pixels 151-31, 151-32 and 151-33.

Also show in FIG. 2 is an X-Y table 210 (or other conveyor mechanism), which is another part of system 100 that moves a sample S relative to sensor 150 in a manner similar to that used in conventional TDI imaging systems. Note that FIG. 2 shows a small portion of sample S (i.e., a defect region DR that includes a small hole or crack in the sample surface), and depicts relative movement of defect region DR as sample S moves relative to sensor 150 during time periods t1 to t9 (i.e., sample "S(t1)" shows defect region DR at an initial time t1, and sample "S(t9)" shows defect region DR at a final time t9). Incident light directed onto defect region DR during each of the nine time periods (indicated by dashed arrows IL(t1) to IL(t9)), and light reflected from defect region DR during each of the nine time periods (indicate by dashed arrows RL(t1) to RL(t9)) is directed onto sensor 150 during the TDI process. Due to relative movement of the sample at the same rate at which corresponding image charge C1 is transferred along column CL1, reflected light RL(t1) to RL(t9) is directed onto each pixel 151-11 to 151-91 such that light received during each time period is integrated with image charge C1 as it transfers down column CL1. That is, light RL(t1) reflected from the defect region DR during first time period t1 generates a "first" collected charge C1(t1) in pixel 151-11. Image charge C1(t1) is then transferred to pixel 151-21 at the end of time period t1 (the beginning of time period t2), and light RL(t2) reflected from the defect region DR during second time period t2 is integrated with transferred charge C1(t1) to generate collected charge C1(t2) in pixel 151-12. Image charge C1(t1) is then transferred to pixel 151-31 and integrated with reflected light RL(t3) during time t3 to generate image charge RL(t3), which is then transferred to pixel 151-41 and integrated with reflected light RL(t4) during time t4 to generate image charge RL(t4), which is then transferred to pixel 151-51 and integrated with reflected light RL(t5) to generate image charge RL(t5), which is then transferred to pixel 151-61 and integrated with reflected light RL(t6) to generate image charge RL(t6), which is then transferred to pixel 151-71 and integrated with reflected light RL(t7) to generate image charge RL(t7), which is then transferred to pixel 151-81 and integrated with reflected light RL(t8) to generate image charge RL(t8), which is then transferred to pixel 151-91 and integrated with reflected light RL(t9) to generate final image charge RL(t9). After time period t9, final charge C1(t9) is transferred from pixel 151-91 to readout amplifiers 155 for transmission off of sensor 150 to readout electronics using knows techniques.

In accordance with an aspect of the invention, due to the variable readout clock signal amplitudes mentioned above, each image charge generation/transfer process involves at least one instance in which the collected charge is transferred from a pixel controlled by readout clock signals having a lower amplitude to a next-sequential pixel controlled by readout clock signals having a higher amplitude. For example, as indicated in FIGS. 1 and 2, due to use of the staircase clock distribution, the readout clock signal amplitude change between pixels occurs twice. The first amplitude change occurs when image charge C1(t3) is transferred from pixel 151-31, which is controlled by readout clock signals P1V1 to P3V1 having amplitude A1, to pixel 151-41, which is controlled by readout clock signals P1V2 to P3V2 having higher amplitude A2. The second amplitude change occurs when image charge C1(t6) is transferred from pixel 151-36, which is controlled by readout clock signals P1V2 to P3V2 having amplitude A2, to pixel 151-71, which is controlled by readout clock signals P1V3 to P3V3 having higher amplitude A3. The repeated transfer of image charges from a pixel controlled by readout clock signals having a lower (first) amplitude to a pixel controlled by readout clock signals having an incrementally higher (second) amplitude is a characteristic of the present invention, and facilitates the power reduction benefits TDI imaging systems constructed in accordance with the present invention. The number of such amplitude changes is determined by the number of levels (i.e., in systems utilizing staircase clock distribution) or by the number of rows (i.e., in systems implementing a continuous ramp clock distribution).

Figure 3:
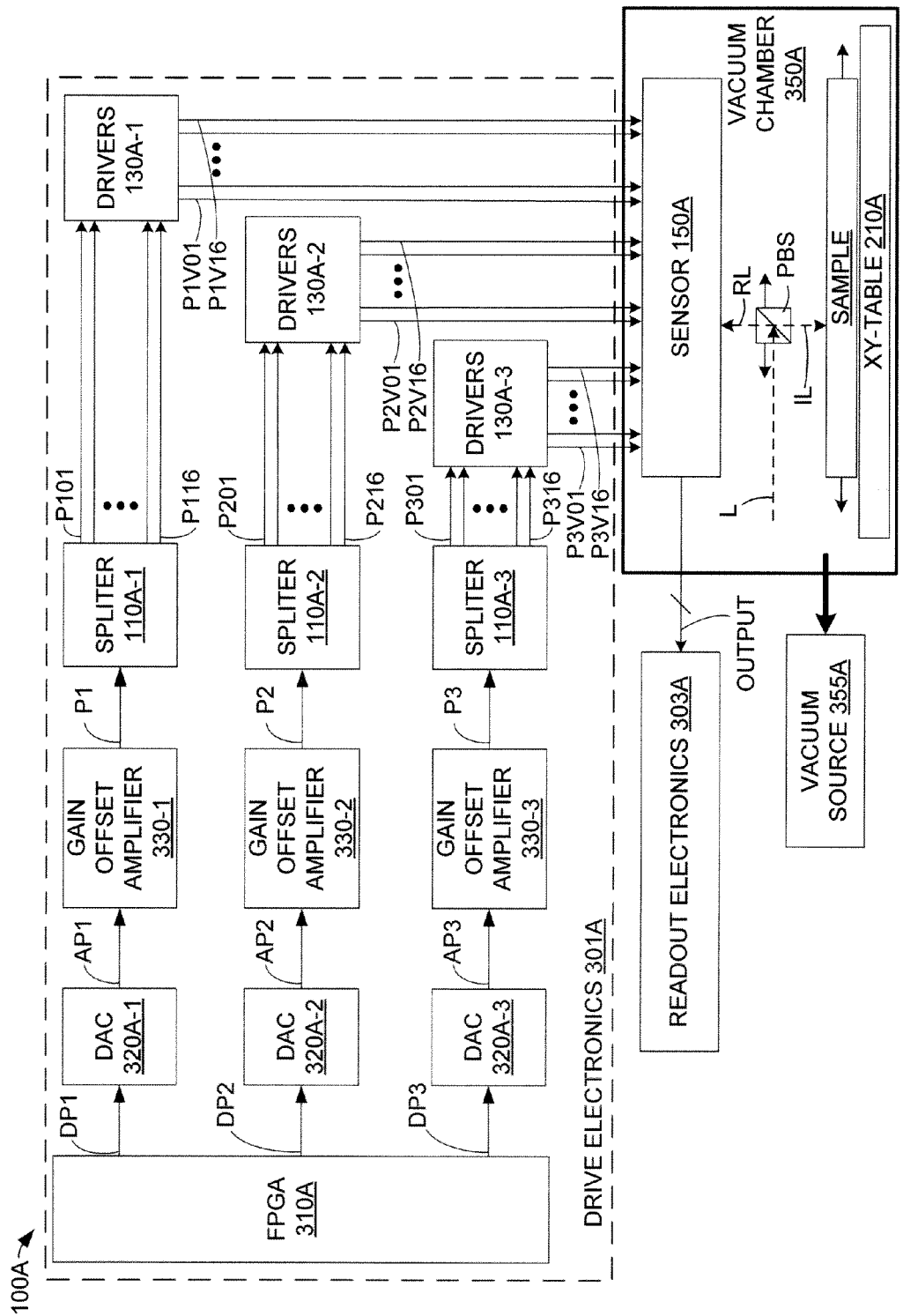
FIG. 3 is a block diagram showing a simplified TDI imaging system time according to a practical embodiment of the present invention.

FIG. 3 is a block diagram showing a TDI imaging system 100A according to a simplified exemplary practical embodiment in which sensor 150A comprises three-gate CCD pixels arranged in a 2048 columns by 1024 rows array, wherein the pixel rows are grouped into sixteen levels (i.e., each level comprises 2048×64 pixels that receive the same set of readout control signals). System 110A therefore includes drive electronics 301A capable of generating forty-eight readout clock signals (i.e., sixteen "phase one" readout clock signals P1V01 to P1V16, sixteen "phase two" readout clock signals P2V01 to P2V16, and sixteen "phase three" readout clock signals P3V01 to P3V16) that are supplied to sensor 150A in sets including one readout clock signal of each phase, where each of the three clocks signals has the same voltage amplitude. In addition, sensor system 100A includes readout electronics that receive and process image charges generated during TDI processes in the manner described above.

According an aspect of the disclosed embodiment, sensor 150A is housed in a vacuum chamber 350A, along with a conveying mechanism (e.g., an XY table 210A) for moving a sample to be inspected, and associated optics (e.g., a polarizing beam splitter PBS and associated lenses (not shown)) that direct incident light IL onto the sample and reflected light RL onto sensor 150A. Note that the source of light L may be located inside vacuum chamber 350A or disposed outside (i.e., with light L passed into vacuum chamber 350A by way of a window). Vacuum chamber 350A facilitates TDI imaging using ultra-high frequency light (e.g., having a wavelength of 13.5 nm) without producing the ionized gas problem associated with conventional systems and methods in which the sample is disposed in a gaseous environment (e.g., air). According to the currently preferred embodiment, in order to minimize heat generation inside vacuum chamber 350A, drive electronics 301A and readout electronics 303A are disposed outside of the vacuum chamber 350A, with readout clock signals P1V01 to P3V16 being transmitted into vacuum chamber 350A by way of suitable connections (e.g., wires or other conductive lines).

In the exemplary practical embodiment shown in FIG. 3, the drive circuitry 301A includes a field-programmable gate array FPGA 310A, digital-to-analog converters (DACs) 320A-1, 320A-2 and 320A-3, optional "first stage" gain offset amplifiers 330A-1, 330A-2 and 330A-3, splitter circuits 110A-1, 110A-2 and 110A-3, and driver circuits 130A-1, 130A-2 and 130A-3 that serve to generate primary phase signals and to then convert the primary phase signals into readout clock signals. FPGA 310A includes look-up tables configured by logic (e.g., stored in look-up tables) that case the FPGA circuit to generate digital phase values DP1, DP2 and DP3 using known techniques. DACs 320A-1 to 320A-3 and optional first stage amplifiers 330A-1 to 330A-3 are coupled to receive digital phase values DP1, DP2 and DP3 from FPGA 310A, and function to respectively convert digital phase values DP1, DP2 and DP3 into primary phase signals P1,P2,P3. In one specific embodiment, DAC 320A-1 is coupled to receive digital phase value DP1, and functions using known techniques to generate associated analog phase signal AP1 having a first phase. Similarly, DACs 320A-2 and 320A-3 are respectively coupled to receive digital phase values DP2 and DP3, and function to generate associated analog phase signals AP2 and AP3, where analog phase signals AP2 and AP3 differ in phase from each other and from analog phase signal AP1. In a specific embodiment, each DAC 320A-1 to 320A-3 comprises a 10-bit 330 MHz DAC such as device ADV7123 produced by Analog Devices of Norwood, Mass., USA. Analog phase signals AP1 to AP3 are then passed to optional first stage amplifiers 330A-1 to 330A-3, which function to amplify and/or signal process the analog phase signals using known techniques to generate primary phase signals P1, P2 and P3 having suitable characteristics. For example, first stage amplifier 330A-1 is coupled to receive associated analog phase signal AP1 from associated DAC 320A-1, and includes circuitry that controls the gain and other characteristics of the received signal such that primary phase signal P1 is generated on its output terminal having desired signal characteristics. Similarly, first stage amplifiers 330A-2 and 330A-3 are coupled to receive associated analog phase signals AP2 and AP3 from associated DACs 320A-2 and 320A-3, respectively, and include circuitry that generate primary phase signals P2 and P3 on their output terminals, respectively. Primary phase signals P1 to P3 are then transmitted to splitter circuits 110A-1 to 110A-3, respectively, where each splitter circuit (e.g., splitter 330A-1) is coupled to receive an associated primary phase signal, and includes circuitry that generates (i.e., "splits" or otherwise duplicates) sixteen identical secondary phase signals that have the same phase and signal characteristics of the received primary phase signal. For example, splitter 330A-1 is coupled to receive the output terminal of amplifier 330A-1, and generates secondary phase signals P101 to P116 in accordance with primary phase signal P1. Similarly, splitters 330A-2 and 330A-3 are coupled to receive primary phase signals P2 and P3, respectively, and generate secondary phase signals P201-P216 and P301 to P316, respectively. Secondary phase signals P101 to P116, P201-P216 and P301 to P316 are then transmitted to driver circuits 130A-1 to 130A-3, each including sixteen gain-controlled drivers such as that described below with reference to FIG. 4, that generate readout control signals P1V01 to P3V16 for transmission to sensor 150A.

Figure 4:
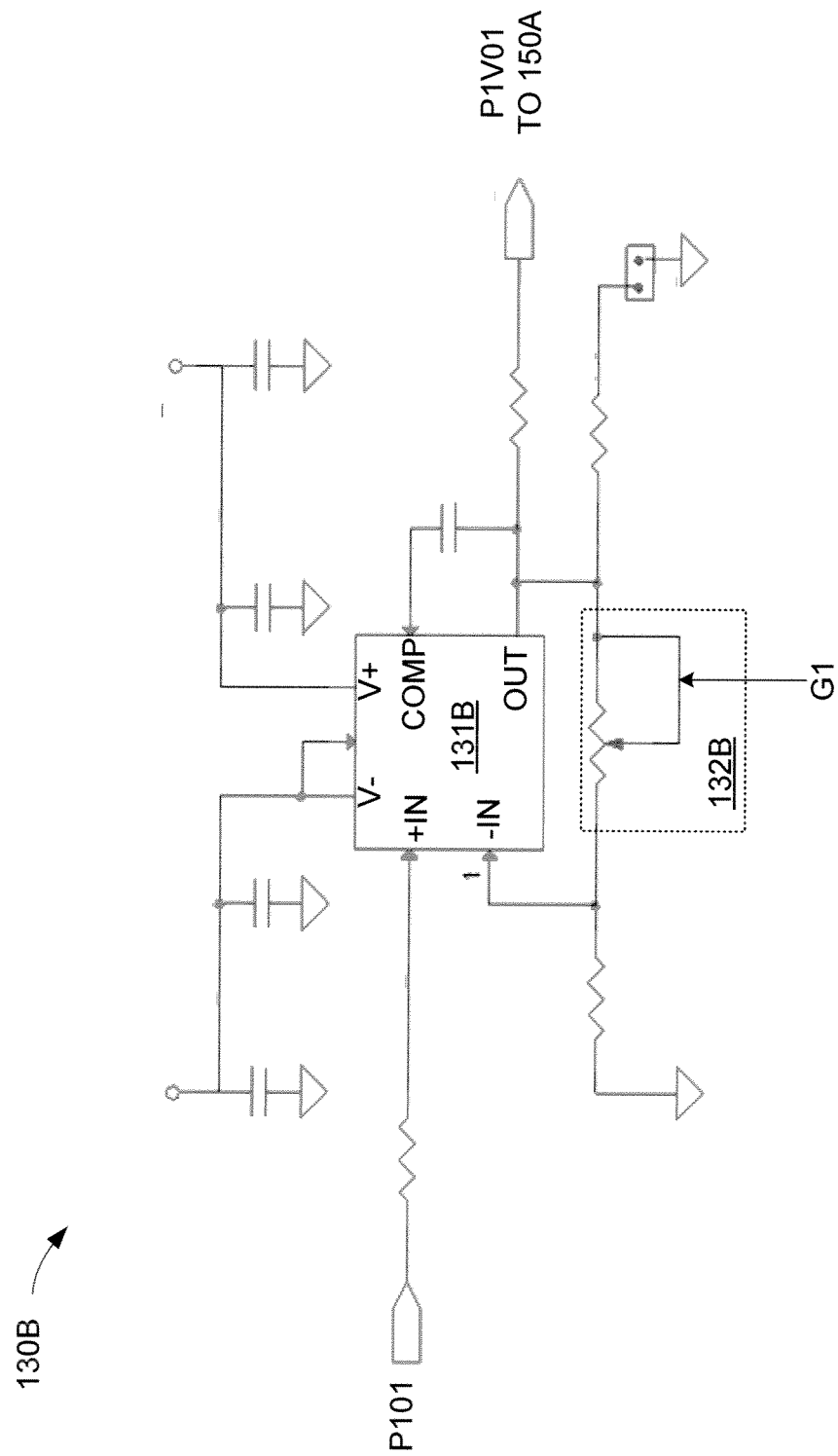
FIG. 4 is a circuit diagram illustrating an exemplary gain-controlled driver circuit utilized to generate variable readout clock signals according to a specific embodiment of the present invention.

FIG. 4 is a circuit diagram illustrating gain-controlled driver (analog driver) 130B utilized by driver circuits 130A-1 to 130A-3 (FIG. 3) according to a specific embodiment of the present invention. Driver 130B generally includes a current feedback amplifier 131B (e.g., an LM7373MRX operational amplifier produced by Texas Instruments of Plano, Tex., USA) and an analog (or digital) rheostat 132B. Amplifier 131B includes a non-inverting (first) input terminal +IN coupled to receive an associated secondary phase signals (e.g., signal P101), an output terminal on which an associated variable amplitude readout clock signal (e.g., signal P1V01) is transmitted, and a non-inverting input terminal –IN. Rheostat 132B is connected between amplifier output terminal OUT and inverting amplifier input terminal –IN (i.e., in the location of a gain-setting resistor), and is configured by an associated control value G1 (e.g., ranging in value from 0 to 15) such that sixteen possible different resistances are generated by rheostat 132B to produce an appropriate gain that causes amplifier 131B to generate the required output voltage amplitude. In system 100A (FIG. 3), driver 130B is replicated forty-eight times to generate readout clock signals P1V01 to P3V16 in order to control every pixel of TDI sensor 150A. The amplifier receives input from the vertical DAC circuit.

Referring again to FIG. 3, each driver circuit 130A-1 to 130A-3 includes sixteen gain-controlled drivers, each identical to driver 130B (FIG. 4), that are configured to generate sixteen readout clock signals that progressively increase in amplitude defined by the expected maximum image charge value (i.e., largest number of photoelectrons stored) in each of the sixteen levels of sensor 150A. Table 1 shows exemplary progressively increasing clock signal amplitudes for each of the sixteen pixel row levels for a typical $V_{FW}=+/-6V$ sinusoidal clock swing.

TABLE 1

| Pixel Level | Amplitude |
| --- | --- |
| Level 1: | +/−0.375 V |
| Level 2: | +/−0.75 V |
| Level 3: | +/−1.125 V |
| Level 4: | +/−1.5 V |
| Level 5: | +/−1.875 V |
| Level 6: | +/−2.25 V |
| Level 7: | +/−2.625 V |
| Level 8: | +/−3 V |
| Level 9: | +/−3.375 V |
| Level 10: | +/−3.75 V |
| Level 11: | +/−4.125 V |
| Level 12: | +/−4.5 V |
| Level 13: | +/−4.875 |
| Level 14: | +/−5.25 V |
| Level 15: | +/−5.625 V |
| Level 16: | +/−6 V |

The embodiments presented herein and the specific aspects illustrated are meant not to be limiting, but may include alternate components while still incorporating the teachings and benefits of the invention, namely the implementation employed to transfer image charges within a TDI sensor using readout clocking signals whose amplitude varies in accordance with column position. While the invention has thus been described in connection with specific embodiments thereof, it will be understood that the invention is capable of further modifications. This application is intended to cover any variations, uses or adaptations of the invention following, in general, the principles of the invention, and including such departures from the present disclosure as come within known and customary practice within the art to which the invention pertains. For example, although the present invention is described with specific reference to TDI CCD sensors having three gates per pixel, the present invention is also applicable to TDI sensors having pixels with two, four or more gates (i.e., using readout clock signals having two, four or more phases). In addition, although the readout clock signals are depicted as continuous (sinusoidal) voltage waveforms (i.e., using a continuous clock mode), which move charge from gate to gate and from pixel to pixel more continuously than square voltage waves, the readout signals may also be generated using a burst mode (i.e., using square voltage waveforms).

The invention claimed is:

1. A Time Delay and Integration (TDI) imaging system, comprising:
    a sensor including an array of pixels arranged in a plurality of rows and a plurality of columns,
    phase signal generating means for generating a plurality of primary phase signals;
    means for splitting each of said plurality of primary phase signals into a plurality of secondary phase signals such that a first said primary phase signal is split into a plurality of identical first secondary phase signals, and a second said primary phase signal is split into a plurality of second secondary phase signals;
    a plurality of drivers configured to generate a plurality of readout clock signals in accordance with said plurality of secondary phase signals, said plurality of drivers being coupled to said sensor such that each row of said pixels receives at least two readout clock signals respectively generated by associated said drivers in accordance with associated secondary phase signals; and
    a gain control circuit configured to control the plurality of drivers such that a first row of pixels disposed adjacent to a first end of said plurality of columns receives first and second readout clock signals having a first amplitude, and a second row of pixels disposed adjacent to a second end of said plurality of columns receives third and fourth readout clock signals having a second amplitude, wherein said second amplitude is greater than said first amplitude.

2. The TDI imaging system of claim 1, wherein said first row of pixels are coupled to receive a first expected maximum image charge amount during a TDI process, and said gain control circuit includes means for controlling a first group of said drivers such that said first amplitude is defined by said first expected maximum image charge amount, and wherein said second row of pixels are coupled to receive a second expected maximum image charge amount during said TDI process, and said gain control circuit includes means for controlling a second group of said drivers such that said second amplitude is defined by said second expected maximum image charge amount.

3. The TDI imaging system of claim 2, wherein gain control circuit includes means for controlling the first and second groups of said drivers such that said second amplitude is at least two times greater than said first amplitude.

4. The TD1 imaging system of claim 1, wherein said gain control circuit further controls the plurality of drivers such that a third row of pixels disposed between said first row and said second row receives a third set of said associated first and second readout clock signals having a third amplitude, wherein said third amplitude is between said second amplitude and said first amplitude.

5. The TDI imaging system of claim 1,
    wherein the plurality of rows are grouped into a plurality of consecutively arranged levels such that each said level includes two or more of said rows, and
    wherein each of the plurality of drivers is coupled to every row of an associated level such that every row of a first level including said first row receives said first readout clock signal generated by an associated first driver.

6. The TDI imaging system of claim 1, further comprising:
    means for moving a sample relative to said sensor such that light reflected from a region of said sample during a first time period generates a first collected charge in a first pixel of each column, and such that second light reflected from said region of said sample during a second time period generates a second collected charge in a second pixel of said each column, wherein said phase signal generating means and said gain control circuit are controlled such that:

said first pixel generates the first collected charge and transfers said first collected charge to said second pixel during said first time period in accordance with said first set of said associated first and second readout clock signals, and said second pixel receives and holds said first collected charge, generates said second collected charge as a sum of said held first collected charge and said second light, and transfers said collected second charge to said third pixel during said second time period in accordance with said second set of said associated first and second readout clock signals having said second amplitude.

7. The TDI imaging system of claim 1, further comprising a vacuum chamber, wherein said phase signal generating means, said means for splitting, and said a plurality of drivers are disposed outside of said vacuum chamber, and wherein said sensor and means for moving a sample relative to said sensor are disposed inside said vacuum chamber.

8. The TDI imaging system of claim 7, wherein said phase signal generating means comprises:

a field programmable gate array (FPGA) configured by logic to generate a plurality of digital phase values; and digital-to-analog converting means coupled to said FPGA for converting each of said plurality of digital phase values into an associated primary phase signal of said plurality of primary phase signals.

9. The TDI imaging system of claim 8, wherein said digital-to-analog converting means comprises:

a plurality of signal digital-to-analog converters (DACs), each said DAC coupled to receive an associated digital phase value of said plurality of digital phase values, and to generate an associated analog phase signal; and a plurality of first stage amplifiers, each said first stage amplifier coupled to receive an associated said analog phase signal from an associated said DAC, and including means for generating an associated said primary phase signal in accordance with said received analog phase signal.

10. The TDI imaging system of claim 8, wherein said means for splitting comprises a plurality of splitter circuits, each said splitter circuit coupled to receive an associated primary phase signal and including means for generating a plurality of identical secondary phase signals in accordance with said received associated primary phase signal.

11. The TDI imaging system of claim 1, wherein each of the plurality of drivers comprises:

a current feedback amplifier having a first input terminal coupled to receive an associated said secondary phase signal, an output terminal, and a second input terminal, and a rheostat connected between the output terminal and the second input terminal; and wherein said gain control circuit comprises means for transmitting a digital control value to each said rheostat of said plurality of drivers.

12. A method for performing a Time Delay and Integration (TDI) sensing process using a sensor including an array of pixels arranged in a plurality of rows and a plurality of columns, the method comprising:

generating a plurality of primary phase signals;

splitting each of said plurality of primary phase signals into a plurality of secondary phase signals such that a first said primary phase signal is split into a plurality of identical first secondary phase signals, and a second said primary phase signal is split into a plurality of second secondary phase signals;

utilizing a plurality of drivers to generate a plurality of readout clock signals in accordance with said plurality of secondary phase signals such that each row of said pixels receives at least an associated first readout clock signal generated by an associated first driver in accordance with an associated said first secondary phase signal, and an associated second readout clock signal signal generated by an associated second driver in accordance with an associated said second secondary phase signal; and controlling the plurality of drivers such that a first row of pixels disposed adjacent to a first end of said plurality of columns receives a first set of said associated first and second readout clock signals having a first amplitude, and a second row of pixels disposed adjacent to a second end of said plurality of columns receives a second set of said associated first and second readout clock signals having a second amplitude, wherein said second amplitude is greater than said first amplitude.

13. The method of claim 12, wherein said first row of pixels are coupled to receive a first expected maximum image charge amount during a TDI process, wherein said second row of pixels are coupled to receive a second expected maximum image charge amount during said TDI process, and wherein controlling the plurality of drivers comprises:

controlling a first group of said drivers such that said first amplitude is defined by said first expected maximum image charge amount, and controlling a second group of said drivers such that said second amplitude is defined by said second expected maximum image charge amount.

14. The method of claim 13, wherein controlling the plurality of drivers further comprises controlling the first and second groups of said drivers such that said second amplitude is at least two times greater than said first amplitude.

15. The method of claim 12, further comprising controlling the plurality of drivers such that a third row of pixels disposed between said first row and said third row receives a third set of said associated first and second readout clock signals having a third amplitude, wherein said third amplitude is between said second amplitude and said first amplitude.

16. The method of claim 12, wherein the plurality of rows are grouped into a series of consecutively arranged levels, each said level including a plurality of adjacent rows, and wherein the method further comprises controlling the plurality of drivers such that every row of a first level receives the same first readout clock signal generated by an associated first driver.

17. The method of claim 12, further comprising:

moving a sample relative to said sensor such that light reflected from a region of said sample during a first time period generates a first collected charge in a first pixel of each column, and such that second light reflected from said region of said sample during a second time period generates a second collected charge in a second pixel of said each column, causing said first pixel to generate the first collected charge and to transfer said first collected charge to said second pixel during said first time period in accordance with said first set of said associated first and second readout clock signals, and causing said second pixel to receive and hold said first collected charge, to generate said second collected charge as a sum of said held first collected charge and said second light, and to transfer said collected second charge to said third pixel during said second time period in accordance with said second set of said associated first and second readout clock signals having said second amplitude.

18. The method of claim 12, further comprising:

disposing said sensor and means for moving a sample relative to said sensor inside a vacuum chamber; and disposing said phase signal generating means, said means for splitting, and said a plurality of drivers outside of said vacuum chamber.

19. The method of claim 17, wherein generating said phase signals comprises:

generating a plurality digital phase values; and converting each of said plurality of digital phase values into an associated primary phase signal of said plurality of primary phase signals, wherein said converting further comprises:

utilizing a plurality of digital-to-analog converters (DACs) to generate a plurality of analog phase signals, each said DAC being coupled to receive an associated digital phase value of said plurality of digital phase values, and generating an associated analog phase signal in response to said received associated digital phase value; and utilizing a plurality of first stage amplifiers to respectively generate said plurality of primary phase signals in accordance with said plurality of analog phase signals.

20. The method of claim 12, wherein each of the plurality of drivers includes:

a current feedback amplifier having a first input terminal coupled to receive an associated said secondary phase signal, an output terminal, and a second input terminal, and a rheostat connected between the output terminal and the second input terminal; and wherein controlling the plurality of drivers comprises transmitting a digital control value to each said rheostat of said plurality of drivers.

* * * * *